United States Patent
Tsai et al.

(10) Patent No.: US 9,833,195 B2
(45) Date of Patent: Dec. 5, 2017

(54) BIOMEDICAL SIGNAL SENSING CIRCUIT

(71) Applicant: National Taiwan University, Taipei (TW)

(72) Inventors: Yi-Lin Tsai, Nantou County (TW);
Fong-Wen Lee, Yilan County (TW);
Chih-Chan Tu, Hsinchu County (TW);
Bang-Cyuan Wang, Taipei (TW);
Tsung-Hsien Lin, Taipei (TW)

(73) Assignee: National Taiwan University, Taipei (TW)

(*) Notice: Subject to any disclaimer, the term of this patent is extended or adjusted under 35 U.S.C. 154(b) by 997 days.

(21) Appl. No.: 14/155,367

(22) Filed: Jan. 15, 2014

(65) Prior Publication Data
US 2015/0141783 A1    May 21, 2015

(30) Foreign Application Priority Data

Nov. 15, 2013  (TW) .............................. 102141664 A

(51) Int. Cl.
*A61B 5/00*    (2006.01)
*A61B 5/04*    (2006.01)

(52) U.S. Cl.
CPC ........ *A61B 5/7225* (2013.01); *A61B 5/04012* (2013.01)

(58) Field of Classification Search
CPC .............. A61B 5/7225; A61B 5/04012; G06F 11/3065; G06F 19/345; G06F 3/044;
(Continued)

(56) References Cited

U.S. PATENT DOCUMENTS 5,919,134 A * 7/1999 Diab .................. A61B 5/14551
600/323
6,161,036 A   12/2000 Matsumura et al.
(Continued)

FOREIGN PATENT DOCUMENTS

TW      201016190      5/2010
TW      I337807        2/2011

OTHER PUBLICATIONS

"Office Action of Taiwan Counterpart Application", dated Mar. 23, 2016, p. 1-p. 3.

*Primary Examiner* — Christopher D Koharski
*Assistant Examiner* — Roland Dinga
(74) *Attorney, Agent, or Firm* — JCIPRNET

(57)  ABSTRACT

A biomedical signal sensing circuit including a first and a second modulation unit, an amplifying unit, a first and a second demodulation unit is provided. The first modulation unit performs a first modulation operation to a first biomedical signal according to a first signal to generate a first modulation signal. The second modulation unit performs a second modulation operation to a second biomedical signal according to a second signal to generate a second modulation signal. The amplifying unit amplifies the first and second modulation signals, and adds the amplified first and second modulation signals to generate a third modulation signal. The first demodulation unit performs a first demodulation operation to the third modulation signal according to the first signal to generate a first sensing signal. The second demodulation unit performs a second demodulation operation to the third modulation signal according to the second signal to generate a second sensing signal.

10 Claims, 2 Drawing Sheets

(58) Field of Classification Search
CPC .. G06F 220/1637; A61K 45/06; G01D 5/145; G01D 5/203
USPC .................................. 600/301; 375/322, 346
See application file for complete search history.

(56) References Cited

U.S. PATENT DOCUMENTS

| | | |
|---|---|---|
| 6,267,723 B1 | 7/2001 | Matsumura et al. |
| 2001/0002206 A1* | 5/2001 | Diab .................. A61B 5/14551 375/322 |

* cited by examiner

BIOMEDICAL SIGNAL SENSING CIRCUIT

CROSS-REFERENCE TO RELATED APPLICATION

This application claims the priority benefit of Taiwan application serial no. 102141664, filed on Nov. 15, 2013. The entirety of the above-mentioned patent application is hereby incorporated by reference herein and made a part of this specification.

BACKGROUND

Technical Field

The invention relates to a sensing circuit. Particularly, the invention relates to a biomedical signal sensing circuit.

Related Art

Along with development of technology and progress of the times, people pay more and more attention to personal health, and various health-related industries are quickly developed. In order to accurately grasp various biomedical signals on human body, various manufactures have developed a wide range of instruments for measuring biomedical signals, for example, an electrocardiograph (ECG) machine, an electroencephalogram (EEG) machine, etc.

However, in a current biomedical signal sensing circuit, when a plurality of biomedical signals are simultaneously sensed, a plurality of independently operated sensing circuit has to be used for sensing. Since each of the sensing circuits has a little mismatch, outputs of the sensing circuits have to be summed and fed back to input terminals of the sensing circuits according to a common-mode feedback method, so as to increase a common-mode rejection ratio (CMRR). However, such method not only wastes a chip fabrication area, but also causes extra power consumption.

SUMMARY

The invention provides a biomedical signal sensing circuit including a first modulation unit, a second modulation unit, an amplifying unit, a first demodulation unit and a second demodulation unit. The first modulation unit receives a first biomedical signal, and performs a first modulation operation to the first biomedical signal according to a first signal to generate a first modulation signal. The second modulation unit receives a second biomedical signal, and performs a second modulation operation to the second biomedical signal according to a second signal to generate a second modulation signal. The second signal is orthogonal to the first signal. The amplifying unit is coupled to the first modulation unit and the second modulation unit, and amplifies the first modulation signal and the second modulation signal, and adds the amplified first and second modulation signals to generate a third modulation signal. The first demodulation unit is coupled to the amplifying unit, and performs a first demodulation operation to the third modulation signal according to the first signal to generate a first sensing signal. The second demodulation unit is coupled to the amplifying unit, and performs a second demodulation operation to the third modulation signal according to the second signal to generate a second sensing signal.

In an embodiment of the invention, the first modulation unit includes a first multiplier, and the first multiplier multiplies the first biomedical signal with the first signal to generate the first modulation signal. The second modulation unit includes a second multiplier, and the second multiplier multiplies the second biomedical signal with the second signal to generate the second modulation signal.

In an embodiment of the invention, the first signal is a sine wave, and the second signal is a cosine wave orthogonal to the sine wave.

In an embodiment of the invention, the amplifying unit includes a first capacitor, a second capacitor, a third capacitor and an operational amplifier. The first capacitor has a first terminal and a second terminal. The first terminal of the first capacitor receives the first modulation signal. The second capacitor has a first terminal and a second terminal. The first terminal of the second capacitor receives the second modulation signal. The third capacitor has a first terminal and a second terminal. The first terminal of the third capacitor is coupled to the second terminal of the first capacitor and the second terminal of the second capacitor. The operational amplifier has a first input terminal, a second input terminal and an output terminal. The first input terminal of the operational amplifier is coupled to the second terminal of the first capacitor. The second input terminal of the operational amplifier is coupled to a ground potential. The output terminal of the operational amplifier is coupled to the first demodulation unit and the second demodulation unit.

In an embodiment of the invention, the first modulation signal includes a first signal component and a second signal component. The first signal component is inverted to the second signal component. The second modulation signal includes a third signal component and a fourth signal component. The third signal component is inverted to the fourth signal component. The amplifying unit includes a first capacitor, a second capacitor, a third capacitor, a fourth capacitor, a fifth capacitor, a sixth capacitor and an operational amplifier. The first capacitor has a first terminal and a second terminal. The first terminal of the first capacitor receives the first signal component. The second capacitor has a first terminal and a second terminal. The first terminal of the second capacitor receives the second signal component. The third capacitor has a first terminal and a second terminal. The first terminal of the third capacitor receives the third signal component. The second terminal of the third capacitor is coupled to the second terminal of the first capacitor. The fourth capacitor has a first terminal and a second terminal. The first terminal of the fourth capacitor receives the fourth signal component. The second terminal of the fourth capacitor is coupled to the second terminal of the second capacitor. The fifth capacitor has a first terminal and a second terminal. The first terminal of the fifth capacitor is coupled to the second terminal of the first capacitor. The sixth capacitor has a first terminal and a second terminal. The first terminal of the sixth capacitor is coupled to the second terminal of the second capacitor. The operational amplifier has a first input terminal, a second input terminal, a first output terminal and a second output terminal. The first input terminal of the operational amplifier is coupled to the second terminal of the first capacitor. The second input terminal of the operational amplifier is coupled to the second terminal of the second capacitor. The first output terminal of the operational amplifier is coupled to the second terminal of the fifth capacitor. The second output terminal of the operational amplifier is coupled to the second terminal of the sixth capacitor.

In an embodiment of the invention, the third modulation signal includes a first component and a second component. The first component is inverted to the second component. The first sensing signal includes a third component and a fourth component. The third component is inverted to the fourth component. The second sensing signal includes a fifth component and a sixth component. The fifth component is inverted to the sixth component. The first demodulation unit has a first input terminal, a second input terminal, a third input terminal, a first output terminal and a second output terminal. The first input terminal of the first demodulation unit is coupled to the first output terminal of the operational amplifier to receive the first component. The second input terminal of the first demodulation unit is coupled to the second output terminal of the operational amplifier to receive the second component. The third input terminal of the first demodulation unit receives the first signal. The first output terminal of the first demodulation unit outputs the third component. The second output terminal of the first demodulation unit outputs the fourth component. The second demodulation unit has a first input terminal, a second input terminal, a third input terminal, a first output terminal and a second output terminal. The first input terminal of the second demodulation unit is coupled to the first output terminal of the operational amplifier to receive the first component. The second input terminal of the second demodulation unit is coupled to the second output terminal of the operational amplifier to receive the second component. The third input terminal of the second demodulation unit receives the second signal. The first output terminal of the second demodulation unit outputs the fifth component. The second output terminal of the second demodulation unit outputs the sixth component.

In an embodiment of the invention, the first biomedical signal includes a first differential signal component and a second differential signal component. The first differential signal component is inverted to the second differential signal component. The second biomedical signal includes a third differential signal component and a fourth differential signal component. The third differential signal component is inverted to the fourth differential signal component. The first signal includes a first portion and a second portion. The first portion is inverted to the second portion. The second signal includes a third portion and a fourth portion. The third portion is inverted to the fourth portion. The first modulation unit has a first input terminal, a second input terminal, a third input terminal, a fourth input terminal, a first output terminal and a second output terminal. The first input terminal of the first modulation unit receives the first differential signal component. The second input terminal of the first modulation unit receives the second differential signal component. The third input terminal of the first modulation unit receives the first portion. The fourth input terminal of the first modulation unit receives the second portion. The second modulation unit has a first input terminal, a second input terminal, a third input terminal, a fourth input terminal, a first output terminal and a second output terminal. The first input terminal of the second modulation unit receives the third differential signal component. The second input terminal of the second modulation unit receives the fourth differential signal component. The third input terminal of the second modulation unit receives the third portion. The fourth input terminal of the second modulation unit receives the fourth portion. The first output terminal of the second modulation unit is coupled to the second output terminal of the first modulation unit.

In an embodiment of the invention, the amplifying unit includes a first capacitor, a second capacitor, a third capacitor, a fourth capacitor and an operational amplifier. The first capacitor has a first terminal and a second terminal. The first terminal of the first capacitor is coupled to the first output terminal of the first modulation unit for receiving the first modulation signal. The second capacitor has a first terminal and a second terminal. The first terminal of the second capacitor is coupled to the second output terminal of the second modulation unit for receiving the second modulation signal. The third capacitor has a first terminal and a second terminal. The first terminal of the third capacitor is coupled to the second terminal of the first capacitor. The fourth capacitor has a first terminal and a second terminal. The first terminal of the fourth capacitor is coupled to the second terminal of the second capacitor. The operational amplifier has a first input terminal, a second input terminal, a first output terminal and a second output terminal. The first input terminal of the operational amplifier is coupled to the second terminal of the first capacitor. The second input terminal of the operational amplifier is coupled to the second terminal of the second capacitor. The first output terminal of the operational amplifier is coupled to the second terminal of the third capacitor. The second output terminal of the operational amplifier is coupled to the second terminal of the fourth capacitor.

In an embodiment of the invention, the first modulation unit includes a first transistor, a second transistor, a third transistor and a fourth transistor. The first transistor has a first terminal, a second terminal and a control terminal. The first terminal of the first transistor receives the first differential signal component. The control terminal of the first transistor receives the second portion. The second transistor has a first terminal, a second terminal and a control terminal. The first terminal of the second transistor receives the first differential signal component. The control terminal of the second transistor receives the first portion. The third transistor has a first terminal, a second terminal and a control terminal. The first terminal of the third transistor receives the second differential signal component. The control terminal of the third transistor receives the first portion. The second terminal of the third transistor is coupled to the second terminal of the first transistor. The fourth transistor has a first terminal, a second terminal and a control terminal. The first terminal of the fourth transistor receives the second differential signal component, and the control terminal of the fourth transistor receives the second portion. The second terminal of the fourth transistor is coupled to the second terminal of the second transistor. The second modulation unit includes a fifth transistor, a sixth transistor, a seventh transistor and an eighth transistor. The fifth transistor has a first terminal, a second terminal and a control terminal. The first terminal of the fifth transistor receives the third differential signal component. The control terminal of the fifth transistor receives the fourth portion. The sixth transistor has a first terminal, a second terminal and a control terminal. The first terminal of the sixth transistor receives the third differential signal component. The control terminal of the sixth transistor receives the third portion. The seventh transistor has a first terminal, a second terminal and a control terminal. The first terminal of the seventh transistor receives the fourth differential signal component. The control terminal of the seventh transistor receives the third portion. The second terminal of the seventh transistor is coupled to the second terminal of the fifth transistor. The eighth transistor has a first terminal, a second terminal and a control terminal. The first terminal of the eighth transistor receives the fourth differential signal component. The control terminal of the eighth transistor receives the fourth portion. The second terminal of the eighth transistor is coupled to the second terminal of the sixth transistor.

In an embodiment of the invention, the third modulation signal includes a first component and a second component. The first component is inverted to the second component.

The first sensing signal includes a third component and a fourth component. The third component is inverted to the fourth component. The second sensing signal includes a fifth component and a sixth component. The fifth component is inverted to the sixth component. The first demodulation unit has a first input terminal, a second input terminal, a third input terminal, a fourth input terminal, a first output terminal and a second output terminal. The first input terminal of the first demodulation unit is coupled to the first output terminal of the operational amplifier to receive the first component. The second input terminal of the first demodulation unit is coupled to the second output terminal of the operational amplifier to receive the second component. The third input terminal of the first demodulation unit receives the first portion. The fourth input terminal of the first demodulation unit receives the second portion. The first output terminal of the first demodulation unit outputs the third component. The second output terminal of the first demodulation unit outputs the fourth component. The second demodulation unit has a first input terminal, a second input terminal, a third input terminal, a fourth input terminal, a first output terminal and a second output terminal. The first input terminal of the second demodulation unit is coupled to the first output terminal of the operational amplifier to receive the first component. The second input terminal of the second demodulation unit is coupled to the second output terminal of the operational amplifier to receive the second component. The third input terminal of the second demodulation unit receives the third portion. The fourth input terminal of the second demodulation unit receives the fourth portion. The first output terminal of the second demodulation unit outputs the fifth component. The second output terminal of the second demodulation unit outputs the sixth component.

In an embodiment of the invention, the first demodulation unit includes a ninth transistor, a tenth transistor, an eleventh transistor and a twelfth transistor. The ninth transistor has a first terminal, a second terminal and a control terminal. The first terminal of the ninth transistor receives the first component. The control terminal of the ninth transistor receives the second portion. The tenth transistor has a first terminal, a second terminal and a control terminal. The first terminal of the tenth transistor receives the first component. The control terminal of the tenth transistor receives the first portion. The eleventh transistor has a first terminal, a second terminal and a control terminal. The first terminal of the eleventh transistor receives the second component. The control terminal of the eleventh transistor receives the first portion. The second terminal of the eleventh transistor is coupled to the second terminal of the ninth transistor. The twelfth transistor has a first terminal, a second terminal and a control terminal. The first terminal of the twelfth transistor receives the second component, and the control terminal of the twelfth transistor receives the second portion. The second terminal of the twelfth transistor is coupled to the second terminal of the tenth transistor. The second demodulation unit includes a thirteenth transistor, a fourteenth transistor, a fifteenth transistor and a sixteenth transistor. The thirteenth transistor has a first terminal, a second terminal and a control terminal. The first terminal of the thirteenth transistor receives the first component. The control terminal of the thirteenth transistor receives the fourth portion. The fourteenth transistor has a first terminal, a second terminal and a control terminal. The first terminal of the fourteenth transistor receives the first component. The control terminal of the fourteenth transistor receives the third portion. The fifteenth transistor has a first terminal, a second terminal and a control terminal. The first terminal of the fifteenth transistor receives the second component. The control terminal of the fifteenth transistor receives the third portion. The second terminal of the fifteenth transistor is coupled to the second terminal of the thirteenth transistor. The sixteenth transistor has a first terminal, a second terminal and a control terminal. The first terminal of the sixteenth transistor receives the second component. The control terminal of the sixteenth transistor receives the fourth portion. The second terminal of the sixteenth transistor is coupled to the second terminal of the fourteenth transistor.

According to the above descriptions, the biomedical signal sensing circuit of the invention is capable of simultaneously processing a plurality of biomedical signals through a plurality of modulation units and demodulation units, so as to correspondingly generate a plurality of sensing signals that do not interfere with each other according to the biomedical signals.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

Figure 1:
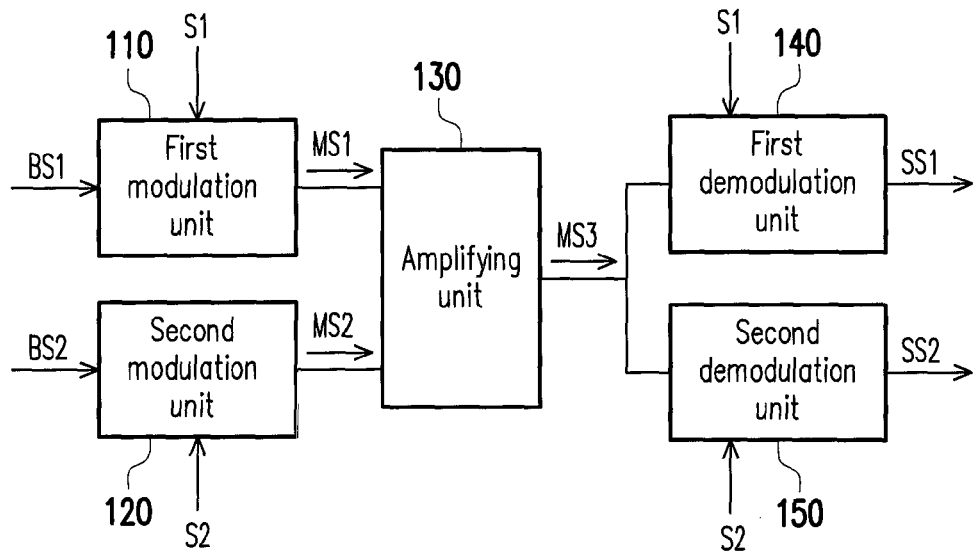
FIG. 1 is a functional block diagram of a biomedical signal sensing circuit according to an embodiment of the invention.

FIG. 1 is a functional block diagram of a biomedical signal sensing circuit according to an embodiment of the invention. In the present embodiment, the biomedical signal sensing circuit 100 includes a first modulation unit 110, a second modulation unit 120, an amplifying unit 130, a first demodulation unit 140 and a second demodulation unit 150.

The first modulation unit 110 receives a first biomedical signal BS1, and performs a first modulation operation to the first biomedical signal BS1 according to a first signal S1 to generate a first modulation signal MS1. In an embodiment, the first modulation unit 110 is, for example, a first multiplier, which multiplies the first biomedical signal BS1 by the first signal S1 to generate the first modulation signal MS1.

The second modulation unit 120 receives a second biomedical signal BS2, and performs a second modulation operation to the second biomedical signal BS2 according to a second signal S2 to generate a second modulation signal MS2. In an embodiment, the second modulation unit 120 is, for example, a second multiplier, which multiplies the second biomedical signal BS2 by the second signal S2 to generate the second modulation signal MS2.

In an embodiment, the first biomedical signal BS1 and the second biomedical signal BS2 are, for example, electrocardiogram (ECG) signals, electroencephalogram (EEG) signals or other physiological measurement signals.

In an embodiment, the second signal S2 is orthogonal to the first signal S1. For example, the first signal S1 is, for example, a sine wave, and the second signal S2 is, for example, a cosine wave orthogonal to the sine wave. Alternatively, in other embodiments, the first signal S1 and the second signal S2 can be respectively implemented by pseudo random codes orthogonal to each other, or other signals orthogonal to each other.

The amplifying unit 130 is coupled to the first modulation unit 110 and the second modulation unit 120. The amplifying unit 130 amplifies the first modulation signal MS1 and the second modulation signal MS2, and adds the amplified first and second modulation signals MS1 and MS2 to generate a third modulation signal MS3. The first demodulation unit 140 is coupled to the amplifying unit 130, and performs a first demodulation operation to the third modulation signal MS3 according to the first signal S1 to generate a first sensing signal SS1. The second demodulation unit 150 is coupled to the amplifying unit 130, and performs a second demodulation operation to the third modulation signal MS3 according to the second signal S2 to generate a second sensing signal SS2.

Since the first signal S1 and the second signal S2 are orthogonal to each other, even if the third modulation signal MS3 includes the added and amplified first and second modulation signals MS1 and MS2, the first demodulation unit 140 and the second demodulation unit 150 can still eliminate an influence of the other modulation signal when performing the first and second demodulation operations, so as to obtain a correct measuring result. For example, when the first demodulation unit 140 performs the first demodulation operation to the third modulation signal MS3 according to the first signal S1, since the first signal S1 is orthogonal to a component of the second signal S2 in the second modulation signal MS2, the first demodulation unit 140 can eliminate the influence of the second modulation signal MS2 from the third modulation signal MS3, so as to generate the first sensing signal SS1 not including the component related to the second modulation signal MS2. On the other hand, when the second demodulation unit 150 performs the second demodulation operation to the third modulation signal MS3 according to the second signal S2, since the second signal S2 is orthogonal to a component of the first signal S1 in the first modulation signal MS1, the second demodulation unit 150 can eliminate the influence of the first modulation signal MS1 from the third modulation signal MS3, so as to generate the second sensing signal SS2 not including the component related to the first modulation signal MS1.

According to another aspect, since the first signal S1 and the second signal S2 are orthogonal to each other, the biomedical signal sensing circuit 100 can process a plurality of biomedical signals simultaneously by only including the single amplifying unit 130, such that the biomedical signal sensing circuit 100 may achieve a smaller volume and lower implementation cost.

Moreover, those skilled in the art should understand that the biomedical signal sensing circuit 100 may also include other modulation units and corresponding demodulation units. In this case, as long as the signals (for example, the first signal S1 and the second signal S2) according which each of the modulation units and the corresponding demodulation unit perform the modulation operation and the demodulation operation are orthogonal to each other, the biomedical signal sensing circuit 100 can simultaneously receive a plurality of biomedical signals, and correspondingly generate a plurality of sensing signals that do not influence each other.

Figure 2:
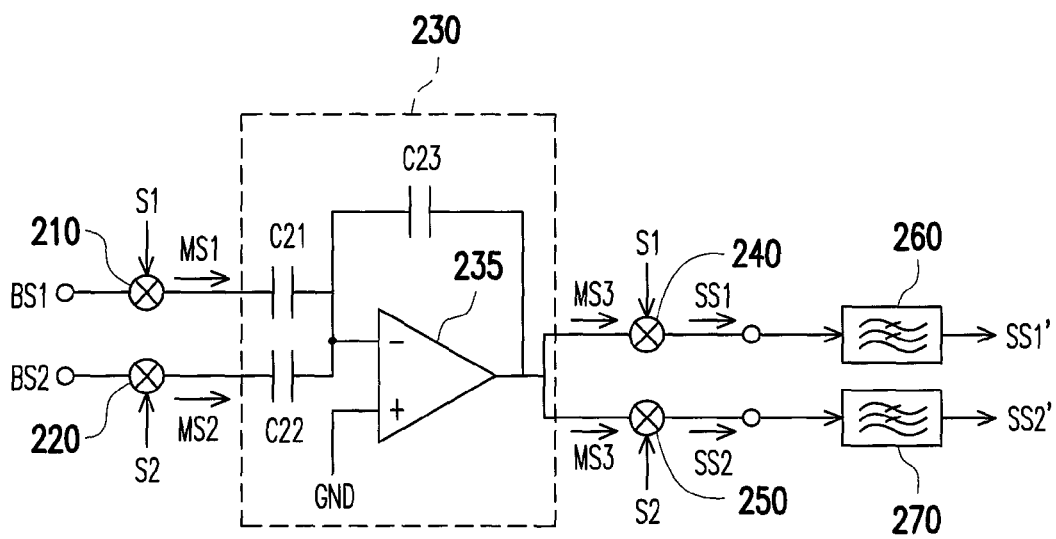
FIG. 2 is a schematic diagram of a biomedical signal sensing circuit according to the embodiment of FIG. 1.

FIG. 2 is a schematic diagram of a biomedical signal sensing circuit according to the embodiment of FIG. 1. In the present embodiment, the biomedical signal sensing circuit 200 includes a first modulation unit 210, a second modulation unit 220, an amplifying unit 230, a first demodulation unit 240 and a second demodulation unit 250. The first modulation unit 210, the second modulation unit 220, the first demodulation unit 240 and the second demodulation unit 250 can be respectively implemented by multipliers, though the invention is not limited thereto.

The first modulation unit 210 receives the first biomedical signal BS1, and multiplies the first biomedical signal BS1 by the first signal S1 to generate the first modulation signal MS1, and the second modulation unit 220 receives the second biomedical signal BS2, and multiplies the second biomedical signal BS2 by the second signal S2 to generate the second modulation signal MS2.

The amplifying unit 230 includes a first capacitor C21, a second capacitor C22, a third capacitor C23 and an operational amplifier 235. The first capacitor C21 has a first terminal and a second terminal. The first terminal of the first capacitor C21 receives the first modulation signal MS1. The second capacitor C22 has a first terminal and a second terminal. The first terminal of the second capacitor C22 receives the second modulation signal MS2. The third capacitor C23 has a first terminal and a second terminal. The first terminal of the third capacitor C23 is coupled to the second terminal of the first capacitor C21 and the second terminal of the second capacitor C22. The operational amplifier 235 has a first input terminal, a second input terminal and an output terminal. The first input terminal of the operational amplifier 235 is coupled to the second terminal of the first capacitor C21. The second input terminal of the operational amplifier 235 is coupled to a ground potential GND. The output terminal of the operational amplifier 235 is coupled to the first demodulation unit 240 and the second demodulation unit 250.

In detail, the first modulation signal MS1 and the second modulation signal MS2 can be respectively a first voltage signal and a second voltage signal, and the two voltage signals can be respectively converted into a first current signal and a second current signal by the first capacitor C21 and the second capacitor C22. Then, the two current signals can be added to produce a third current signal at the second terminal of the first capacitor C21 (i.e. the second terminal of the second capacitor C22). Thereafter, the operational amplifier 235 amplifies the third current signal to generate the third modulation signal MS3.

Then, the first demodulation unit 240 receives the third modulation signal MS3 and multiplies the same by the first signal S1 to generate the first sensing signal SS1. Moreover, the second demodulation unit 250 receives the third modulation signal MS3 and multiplies the same by the second signal S2 to generate the second sensing signal SS2.

Similar to the instructions of the embodiment of FIG. 1, since the first signal S1 is orthogonal to the second signal S2, when the first demodulation unit 240 multiplies the third modulation signal MS3 by the first signal S1, the first demodulation unit 240 can correspondingly eliminate the component related to the second modulation signal MS2 from the third modulation signal MS3, so as to generate the first sensing signal SS1 not including the component related to the second modulation signal MS2. Similarly, the second demodulation unit 250 can also generate the second sensing signal SS2 not including the component related to the first modulation signal MS1, and details thereof are not repeated.

In other embodiments, the biomedical signal sensing circuit 200 may further include a first low-pass filter 260 and a second low-pass filter 270. The first low-pass filter 260 is coupled to the first demodulation unit 240, and performs a first low-pass filtering operation to the first sensing signal SS1 to generate a first filtering signal SS1'. The second low-pass filter 270 is coupled to the second demodulation unit 250, and performs a second low-pass filtering operation to the second sensing signal SS2 to generate a second filtering signal SS2'.

In other embodiments, various devices in the biomedical signal sensing circuit can also be implemented by differential circuits, so as to further decrease a noise, for example, a common-mode noise, etc.

Figure 3:
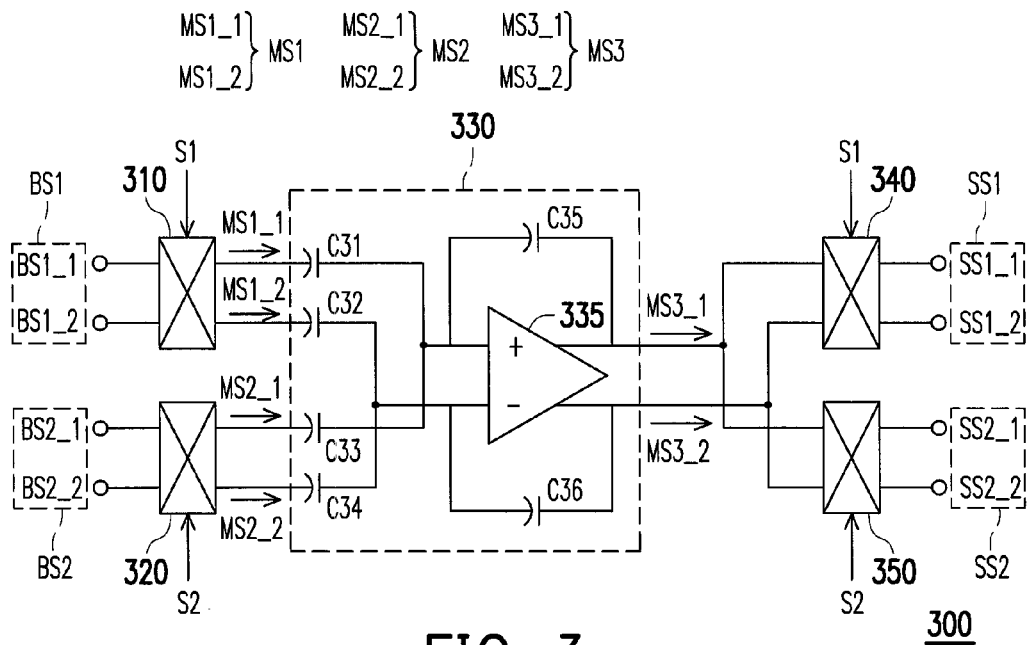
FIG. 3 is a schematic diagram of a biomedical signal sensing circuit according to the embodiment of FIG. 1.

FIG. 3 is a schematic diagram of a biomedical signal sensing circuit according to the embodiment of FIG. 1. In the present embodiment, the biomedical signal sensing circuit 300 includes a first modulation unit 310, a second modulation unit 320, an amplifying unit 330, a first demodulation unit 340 and a second demodulation unit 350.

In the present embodiment, the first biomedical signal BS1 includes a first differential signal component BS1_1 and a second differential signal component BS1_2. The first differential signal component BS1_1 is inverted to the second differential signal component BS1_2. The second biomedical signal BS2 includes a third differential signal component BS2_1 and a fourth differential signal component BS2_2. The third differential signal component BS2_1 is inverted to the fourth differential signal component BS2_2.

The first modulation unit 310 has a first input terminal, a second input terminal, a third input terminal, a first output terminal and a second output terminal. The first input terminal of the first modulation unit 310 receives the first differential signal BS1_1. The second input terminal of the first modulation unit 310 receives the second differential signal BS1_2. The third input terminal of the first modulation unit 310 receives the first signal. The second modulation unit 320 has a first input terminal, a second input terminal, a third input terminal, a first output terminal and a second output terminal. The first input terminal of the second modulation unit 320 receives the third differential signal BS2_1. The second input terminal of the second modulation unit 320 receives the fourth differential signal BS2_2. The third input terminal of the second modulation unit 320 receives the second signal.

In the present embodiment, the first modulation signal MS1 includes a first signal component MS1_1 and a second signal component MS1_2. The first signal component MS1_1 is inverted to the second signal component MS1_2. The second modulation signal MS2 includes a third signal component MS2_1 and a fourth signal component MS2_2. The third signal component MS2_1 is inverted to the fourth signal component MS2_2.

The amplifying unit 330 includes a first capacitor C31, a second capacitor C32, a third capacitor C33, a fourth capacitor C34, a fifth capacitor C35, a sixth capacitor C36 and an operational amplifier 335. The first capacitor C31 has a first terminal and a second terminal. The first terminal of the first capacitor C31 receives the first signal component MS1_1. The second capacitor C32 has a first terminal and a second terminal. The first terminal of the second capacitor C32 receives the second signal component MS1_2. The third capacitor C33 has a first terminal and a second terminal. The first terminal of the third capacitor C33 receives the third signal component MS2_1. The second terminal of the third capacitor C33 is coupled to the second terminal of the first capacitor C31. The fourth capacitor C34 has a first terminal and a second terminal. The first terminal of the fourth capacitor C34 receives the fourth signal component MS2_2. The second terminal of the fourth capacitor C34 is coupled to the second terminal of the second capacitor C32. The fifth capacitor C35 has a first terminal and a second terminal. The first terminal of the fifth capacitor C35 is coupled to the second terminal of the first capacitor C31. The sixth capacitor C36 has a first terminal and a second terminal. The first terminal of the sixth capacitor C36 is coupled to the second terminal of the second capacitor C32. The operational amplifier 335 has a first input terminal, a second input terminal, a first output terminal and a second output terminal. The first input terminal of the operational amplifier 335 is coupled to the second terminal of the first capacitor C31. The second input terminal of the operational amplifier 335 is coupled to the second terminal of the second capacitor C32. The first output terminal of the operational amplifier 335 is coupled to the second terminal of the fifth capacitor C35. The second output terminal of the operational amplifier 335 is coupled to the second terminal of the sixth capacitor C36.

The third modulation signal MS3 includes a first component MS3_1 and a second component MS3_2. The first component MS3_1 is inverted to the second component MS3_2. The first sensing signal SS1 includes a third component SS1_1 and a fourth component SS1_2. The third component SS1_1 is inverted to the fourth component SS1_2. The second sensing signal SS2 includes a fifth component SS2_1 and a sixth component SS2_2. The fifth component SS2_1 is inverted to the sixth component SS2_2.

The first demodulation unit 340 has a first input terminal, a second input terminal, a third input terminal, a first output terminal and a second output terminal. The first input terminal of the first demodulation unit 340 is coupled to the first output terminal of the operational amplifier 335 to receive the first component MS3_1. The second input terminal of the first demodulation unit 340 is coupled to the second output terminal of the operational amplifier 335 to receive the second component MS3_2. The third input terminal of the first demodulation unit 340 receives the first signal S1. The first output terminal of the first demodulation unit 340 outputs the third component SS1_1. The second output terminal of the first demodulation unit 340 outputs the fourth component SS1_2. The second demodulation unit 350 has a first input terminal, a second input terminal, a third input terminal, a first output terminal and a second output terminal. The first input terminal of the second demodulation unit 350 is coupled to the first output terminal of the operational amplifier 335 to receive the first component MS3_1. The second input terminal of the second demodulation unit 350 is coupled to the second output terminal of the operational amplifier 335 to receive the second component MS3_2. The third input terminal of the second demodulation unit 350 receives the second signal S2. The first output terminal of the second demodulation unit 350 outputs the fifth component SS2_1. The second output terminal of the second demodulation unit 350 outputs the sixth component SS2_2.

Compared to the biomedical signal sensing circuit 200 in the embodiment of FIG. 2, besides that the biomedical signal sensing circuit 300 of the present embodiment can correctly generate the first sensing signal SS1 and the second sensing signal SS2 that do not interfere with each other, a whole common-mode noise can be further decreased.

In other embodiments, the designer can decrease the required number of the capacitors by adjusting a circuit connection method of the biomedical signal sensing circuit, so as to decrease a whole circuit area and the manufacturing cost.

Figure 4:
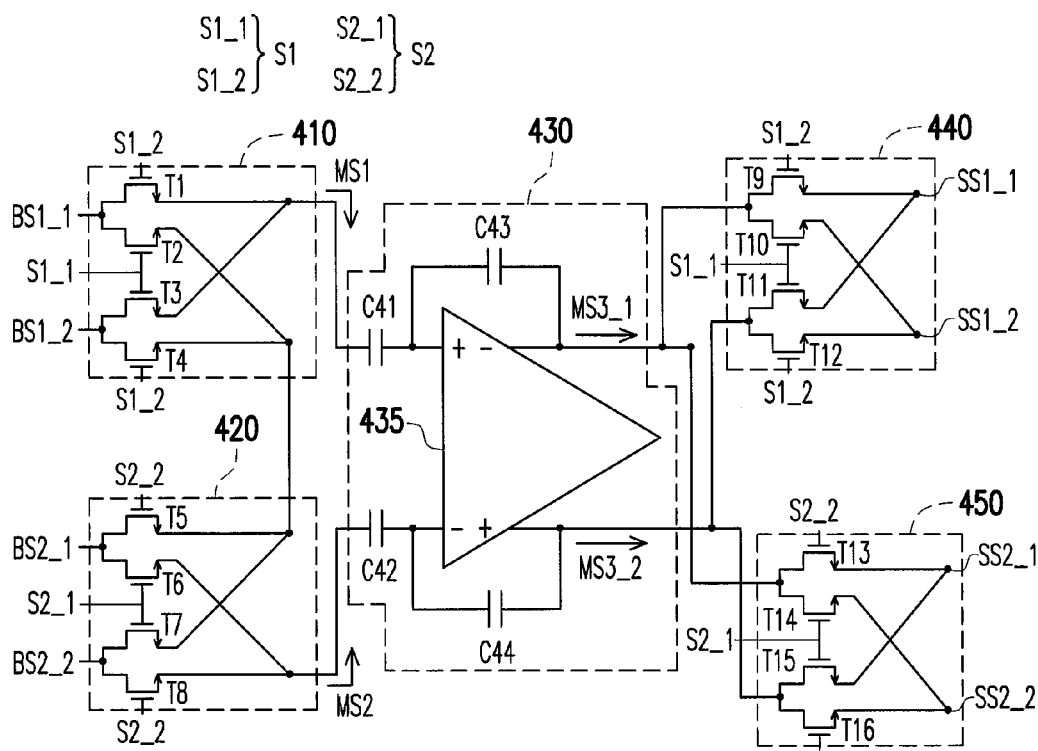
FIG. 4 is a schematic diagram of a biomedical signal sensing circuit according to the embodiment of FIG. 1.

Referring to FIG. 4, FIG. 4 is a schematic diagram of a biomedical signal sensing circuit according to an embodiment of the invention. As that shown in FIG. 4, the biomedical signal sensing circuit 400 includes a first modulation unit 410, a second modulation unit 420, an amplifying unit 430, a first demodulation unit 440 and a second demodulation unit 450.

In the present embodiment, the first biomedical signal BS1 includes a first differential signal component BS1_1 and a second differential signal component BS1_2. The first differential signal component BS1_1 is inverted to the second differential signal component BS1_2. The second biomedical signal BS2 includes a third differential signal component BS2_1 and a fourth differential signal component BS2_2. The third differential signal component BS2_1 is inverted to the fourth differential signal component BS2_2. The first signal S1 includes a first portion S1_1 and a second portion S1_2. The first portion S1_1 is inverted to the second portion S1_2. The second signal S2 includes a third portion S2_1 and a fourth portion S2_2. The third portion S2_1 is inverted to the fourth portion S2_2.

The first modulation unit 410 has a first input terminal, a second input terminal, a third input terminal, a fourth input terminal, a first output terminal and a second output terminal. The first input terminal of the first modulation unit 410 receives the first differential signal BS1_1. The second input terminal of the first modulation unit 410 receives the second differential signal BS1_2. The third input terminal of the first modulation unit 410 receives the first portion S1_1. The fourth input terminal of the first modulation unit 410 receives the second portion S1_2.

The second modulation unit 420 has a first input terminal, a second input terminal, a third input terminal, a fourth input terminal, a first output terminal and a second output terminal. The first input terminal of the second modulation unit 420 receives the third differential signal BS2_1. The second input terminal of the second modulation unit 420 receives the fourth differential signal BS2_2. The third input terminal of the second modulation unit 420 receives the third portion S2_1. The fourth input terminal of the second modulation unit 420 receives the fourth portion S2_2. The first output terminal of the second modulation unit 420 is coupled to the second output terminal of the first modulation unit 410.

The amplifying unit 430 includes a first capacitor C41, a second capacitor C42, a third capacitor C43, a fourth capacitor C44 and an operational amplifier 435. The first capacitor C41 has a first terminal and a second terminal. The first terminal of the first capacitor C41 is coupled to the first output terminal of the first modulation unit 410 for receiving the first modulation signal MS1. The second capacitor C42 has a first terminal and a second terminal. The first terminal of the second capacitor C42 is coupled to the second output terminal of the second modulation unit 420 for receiving the second modulation signal MS2. The third capacitor C43 has a first terminal and a second terminal. The first terminal of the third capacitor C43 is coupled to the second terminal of the first capacitor C41. The fourth capacitor C44 has a first terminal and a second terminal. The first terminal of the fourth capacitor C44 is coupled to the second terminal of the second capacitor C42. The operational amplifier 435 has a first input terminal, a second input terminal, a first output terminal and a second output terminal. The first input terminal of the operational amplifier 435 is coupled to the second terminal of the first capacitor C41. The second input terminal of the operational amplifier 435 is coupled to the second terminal of the second capacitor C42. The first output terminal of the operational amplifier 435 is coupled to the second terminal of the third capacitor C43. The second output terminal of the operational amplifier 435 is coupled to the second terminal of the fourth capacitor C44.

In the present embodiment, the first modulation unit 410 includes a first transistor T1, a second transistor T2, a third transistor T3 and a fourth transistor T4. The first transistor T1 has a first terminal, a second terminal and a control terminal. The first terminal of the first transistor T1 receives the first differential signal component BS1_1. The control terminal of the first transistor T1 receives the second portion S1_2. The second transistor T2 has a first terminal, a second terminal and a control terminal. The first terminal of the second transistor T2 receives the first differential signal component BS1_1. The control terminal of the second transistor T2 receives the first portion S1_1. The third transistor T3 has a first terminal, a second terminal and a control terminal. The first terminal of the third transistor T3 receives the second differential signal component BS1_2. The control terminal of the third transistor T3 receives the first portion S1_1. The second terminal of the third transistor T3 is coupled to the second terminal of the first transistor T1. The fourth transistor T4 has a first terminal, a second terminal and a control terminal. The first terminal of the fourth transistor T4 receives the second differential signal component BS1_2, and the control terminal of the fourth transistor T4 receives the second portion S1_2. The second terminal of the fourth transistor T4 is coupled to the second terminal of the second transistor T2.

The second modulation unit 420 includes a fifth transistor T5, a sixth transistor T6, a seventh transistor T7 and an eighth transistor T8. The fifth transistor T5 has a first terminal, a second terminal and a control terminal. The first terminal of the fifth transistor T5 receives the third differential signal component BS2_1. The control terminal of the fifth transistor T5 receives the fourth portion S2_2. The sixth transistor T6 has a first terminal, a second terminal and a control terminal. The first terminal of the sixth transistor T6 receives the third differential signal component BS2_1. The control terminal of the sixth transistor T6 receives the third portion S2_1. The seventh transistor T7 has a first terminal, a second terminal and a control terminal. The first terminal of the seventh transistor T7 receives the fourth differential signal component BS2_2. The control terminal of the seventh transistor T7 receives the third portion S2_1. The second terminal of the seventh transistor T7 is coupled to the second terminal of the fifth transistor T5. The eighth transistor T8 has a first terminal, a second terminal and a control terminal. The first terminal of the eighth transistor T8 receives the fourth differential signal component BS2_2. The control terminal of the eighth transistor T8 receives the fourth portion S2_2. The second terminal of the eighth transistor T8 is coupled to the second terminal of the sixth transistor T6.

The third modulation signal MS3 includes a first component MS3_1 and a second component MS3_2. The first component MS3_1 is inverted to the second component MS3_2. The first sensing signal SS1 includes a third component SS1_1 and a fourth component SS1_2. The third component SS1_1 is inverted to the fourth component SS1_2. The second sensing signal SS2 includes a fifth component SS2_1 and a sixth component SS2_2. The fifth component SS2_1 is inverted to the sixth component SS2_2.

The first demodulation unit 440 has a first input terminal, a second input terminal, a third input terminal, a fourth input terminal, a first output terminal and a second output terminal. The first input terminal of the first demodulation unit 440 is coupled to the first output terminal of the operational amplifier 435 to receive the first component MS3_1. The second input terminal of the first demodulation unit 440 is coupled to the second output terminal of the operational amplifier 435 to receive the second component MS3_2. The third input terminal of the first demodulation unit 440 receives the first portion S1_1. The fourth input terminal of the first demodulation unit 440 receives the second portion S1_2. The first output terminal of the first demodulation unit 440 outputs the third component SS1_1. The second output terminal of the first demodulation unit 440 outputs the fourth component SS1_2.

The second demodulation unit 450 has a first input terminal, a second input terminal, a third input terminal, a fourth input terminal, a first output terminal and a second output terminal. The first input terminal of the second demodulation unit 450 is coupled to the first output terminal of the operational amplifier 435 to receive the first component MS3_1. The second input terminal of the second demodulation unit 450 is coupled to the second output terminal of the operational amplifier 435 to receive the second component MS3_2. The third input terminal of the second demodulation unit 450 receives the third portion S2_1. The fourth input terminal of the second demodulation unit 450 receives the fourth portion S2_2. The first output terminal of the second demodulation unit 450 outputs the fifth component SS2_1. The second output terminal of the second demodulation unit 450 outputs the sixth component SS2_2.

The first demodulation unit 440 includes a ninth transistor T9, a tenth transistor T10, an eleventh transistor T11 and a twelfth transistor T12. The ninth transistor T9 has a first terminal, a second terminal and a control terminal. The first terminal of the ninth transistor T9 receives the first component MS3_1. The control terminal of the ninth transistor T9 receives the second portion S1_2. The tenth transistor T10 has a first terminal, a second terminal and a control terminal. The first terminal of the tenth transistor T10 receives the first component MS3_1. The control terminal of the tenth transistor T10 receives the first portion S1_1. The eleventh transistor T11 has a first terminal, a second terminal and a control terminal. The first terminal of the eleventh transistor T11 receives the second component MS3_2. The control terminal of the eleventh transistor T11 receives the first portion S1_1. The second terminal of the eleventh transistor T11 is coupled to the second terminal of the ninth transistor T9. The twelfth transistor T12 has a first terminal, a second terminal and a control terminal. The first terminal of the twelfth transistor T12 receives the second component MS3_2. The control terminal of the twelfth transistor T12 receives the second portion S1_2. The second terminal of the twelfth transistor T12 is coupled to the second terminal of the tenth transistor T10.

The second demodulation unit 450 includes a thirteenth transistor T13, a fourteenth transistor T14, a fifteenth transistor T15 and a sixteenth transistor T16. The thirteenth transistor T13 has a first terminal, a second terminal and a control terminal. The first terminal of the thirteenth transistor T13 receives the first component MS3_1. The control terminal of the thirteenth transistor T13 receives the fourth portion S2_2. The fourteenth transistor T14 has a first terminal, a second terminal and a control terminal. The first terminal of the fourteenth transistor T14 receives the first component MS3_1. The control terminal of the fourteenth transistor T14 receives the third portion S2_1. The fifteenth transistor T15 has a first terminal, a second terminal and a control terminal. The first terminal of the fifteenth transistor T15 receives the second component MS3_2. The control terminal of the fifteenth transistor T15 receives the third portion S2_1. The second terminal of the fifteenth transistor T15 is coupled to the second terminal of the thirteenth transistor T13. The sixteenth transistor T16 has a first terminal, a second terminal and a control terminal. The first terminal of the sixteenth transistor T16 receives the second component MS32. The control terminal of the sixteenth transistor T16 receives the fourth portion S2_2. The second terminal of the sixteenth transistor T16 is coupled to the second terminal of the fourteenth transistor T14.

Compared to the biomedical signal sensing circuit 300 of FIG. 3 that includes six capacitors, the biomedical signal sensing circuit 400 of FIG. 4 can achieve the effect of generating a plurality of sensing signals that do not interfere with each other by only using four capacitors, such that the whole circuit volume and the manufacturing cost are further decreased.

In summary, the biomedical signal sensing circuit of the invention is capable of simultaneously processing a plurality of biomedical signals through a plurality of modulation units and demodulation units, so as to correspondingly generate a plurality of sensing signals that do not interfere with each other according to the biomedical signals. It should be noticed that the biomedical signal sensing circuit of the invention may simultaneously process a plurality of biomedical signals in case that only a single amplifying unit is included, which is different to the conventional biomedical signal sensing circuit that can only process a single biomedical signal at one time. Therefore, compared to the conventional biomedical signal sensing circuit, the biomedical signal sensing circuit of the invention may have a smaller volume and lower implementation cost.

Moreover, since the biomedical signal sensing circuit of the invention is unnecessary to use a plurality of sensing circuits to sense the biomedical signals, mismatch of the sensing circuits is avoided, such that common-mode feedback is avoided, and the power consumption is reduced.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:
1. A biomedical signal sensing circuit, comprising:
a first modulation unit, receiving a first biomedical signal, and performing a first modulation operation to the first biomedical signal according to a first signal to generate a first modulation signal;
a second modulation unit, receiving a second biomedical signal, and performing a second modulation operation to the second biomedical signal according to a second signal to generate a second modulation signal, wherein the second signal is orthogonal to the first signal;
an amplifying unit, coupled to the first modulation unit and the second modulation unit, amplifying the first modulation signal and the second modulation signal, and adding the amplified first modulation signal and second modulation signal to generate a third modulation signal;

a first demodulation unit, coupled to the amplifying unit, and performing a first demodulation operation to the third modulation signal according to the first signal to generate a first sensing signal; and a second demodulation unit, coupled to the amplifying unit, and performing a second demodulation operation to the third modulation signal according to the second signal to generate a second sensing signal, wherein the amplifying unit comprises:

a first capacitor, having a first terminal and a second terminal, wherein the first terminal of the first capacitor receives the first modulation signal;

a second capacitor, having a first terminal and a second terminal, wherein the first terminal of the second capacitor receives the second modulation signal;

a third capacitor, having a first terminal and a second terminal, wherein the first terminal of the third capacitor is coupled to the second terminal of the first capacitor and the second terminal of the second capacitor; and an operational amplifier, having a first input terminal, a second input terminal and an output terminal, wherein the first input terminal of the operational amplifier is coupled to the second terminal of the first capacitor, the second input terminal of the operational amplifier is coupled to a ground potential, and the output terminal of the operational amplifier is coupled to the first demodulation unit and the second demodulation unit.

2. The biomedical signal sensing circuit as claimed in claim 1, wherein the first modulation unit comprises a first multiplier, and the first multiplier multiplies the first biomedical signal with the first signal to generate the first modulation signal, and the second modulation unit comprises a second multiplier, and the second multiplier multiplies the second biomedical signal with the second signal to generate the second modulation signal.

3. The biomedical signal sensing circuit as claimed in claim 1, wherein the first signal is a sine wave, and the second signal is a cosine wave orthogonal to the sine wave.

4. A biomedical signal sensing circuit, comprising:

a first modulation unit, receiving a first biomedical signal, and performing a first modulation operation to the first biomedical signal according to a first signal to generate a first modulation signal;

a second modulation unit, receiving a second biomedical signal, and performing a second modulation operation to the second biomedical signal according to a second signal to generate a second modulation signal, wherein the second signal is orthogonal to the first signal;

an amplifying unit, coupled to the first modulation unit and the second modulation unit, amplifying the first modulation signal and the second modulation signal, and adding the amplified first modulation signal and second modulation signal to generate a third modulation signal;

a first demodulation unit, coupled to the amplifying unit, and performing a first demodulation operation to the third modulation signal according to the first signal to generate a first sensing signal; and a second demodulation unit, coupled to the amplifying unit, and performing a second demodulation operation to the third modulation signal according to the second signal to generate a second sensing signal, wherein the first modulation signal comprises a first signal component and a second signal component, the first signal component is inverted to the second signal component, the second modulation signal comprises a third signal component and a fourth signal component, the third signal component is inverted to the fourth signal component, wherein the amplifying unit comprises:

a first capacitor, having a first terminal and a second terminal, wherein the first terminal of the first capacitor receives the first signal component;

a second capacitor, having a first terminal and a second terminal, wherein the first terminal of the second capacitor receives the second signal component;

a third capacitor, having a first terminal and a second terminal, wherein the first terminal of the third capacitor receives the third signal component, and the second terminal of the third capacitor is coupled to the second terminal of the first capacitor;

a fourth capacitor, having a first terminal and a second terminal, wherein the first terminal of the fourth capacitor receives the fourth signal component, and the second terminal of the fourth capacitor is coupled to the second terminal of the second capacitor;

a fifth capacitor, having a first terminal and a second terminal, wherein the first terminal of the fifth capacitor is coupled to the second terminal of the first capacitor;

a sixth capacitor, having a first terminal and a second terminal, wherein the first terminal of the sixth capacitor is coupled to the second terminal of the second capacitor; and an operational amplifier, having a first input terminal, a second input terminal, a first output terminal and a second output terminal, wherein the first input terminal of the operational amplifier is coupled to the second terminal of the first capacitor, the second input terminal of the operational amplifier is coupled to the second terminal of the second capacitor, the first output terminal of the operational amplifier is coupled to the second terminal of the fifth capacitor, and the second output terminal of the operational amplifier is coupled to the second terminal of the sixth capacitor.

5. The biomedical signal sensing circuit as claimed in claim 4, wherein the third modulation signal comprises a first component and a second component, the first component is inverted to the second component, the first sensing signal comprises a third component and a fourth component, the third component is inverted to the fourth component, the second sensing signal comprises a fifth component and a sixth component, and the fifth component is inverted to the sixth component, wherein the first demodulation unit has a first input terminal, a second input terminal, a third input terminal, a first output terminal and a second output terminal, the first input terminal of the first demodulation unit is coupled to the first output terminal of the operational amplifier to receive the first component, the second input terminal of the first demodulation unit is coupled to the second output terminal of the operational amplifier to receive the second component, the third input terminal of the first demodulation unit receives the first signal, the first output terminal of the first demodulation unit outputs the third component, and the second output terminal of the first demodulation unit outputs the fourth component, wherein the second demodulation unit has a first input terminal, a second input terminal, a third input terminal, a first output terminal and a second output terminal, the first input terminal of the second demodulation unit is coupled to the first output terminal of the operational amplifier to receive the first component, the second input terminal of the second demodulation unit is coupled to the second output terminal of the operational amplifier to receive the second component, the third input terminal of the second demodulation unit receives the second signal, the first output terminal of the second demodulation unit outputs the fifth component, and the second output terminal of the second demodulation unit outputs the sixth component.

6. A biomedical signal sensing circuit, comprising:
a first modulation unit, receiving a first biomedical signal, and performing a first modulation operation to the first biomedical signal according to a first signal to generate a first modulation signal;
a second modulation unit, receiving a second biomedical signal, and performing a second modulation operation to the second biomedical signal according to a second signal to generate a second modulation signal, wherein the second signal is orthogonal to the first signal;
an amplifying unit, coupled to the first modulation unit and the second modulation unit, amplifying the first modulation signal and the second modulation signal, and adding the amplified first modulation signal and second modulation signal to generate a third modulation signal;
a first demodulation unit, coupled to the amplifying unit, and performing a first demodulation operation to the third modulation signal according to the first signal to generate a first sensing signal; and
a second demodulation unit, coupled to the amplifying unit, and performing a second demodulation operation to the third modulation signal according to the second signal to generate a second sensing signal,
wherein the first biomedical signal comprises a first differential signal component and a second differential signal component, the first differential signal component is inverted to the second differential signal component, the second biomedical signal comprises a third differential signal component and a fourth differential signal component, the third differential signal component is inverted to the fourth differential signal component, the first signal comprises a first portion and a second portion, the first portion is inverted to the second portion, the second signal comprises a third portion and a fourth portion, and the third portion is inverted to the fourth portion,
wherein the first modulation unit has a first input terminal, a second input terminal, a third input terminal, a fourth input terminal, a first output terminal and a second output terminal, the first input terminal of the first modulation unit receives the first differential signal component, the second input terminal of the first modulation unit receives the second differential signal component, the third input terminal of the first modulation unit receives the first portion, and the fourth input terminal of the first modulation unit receives the second portion,
wherein the second modulation unit has a first input terminal, a second input terminal, a third input terminal, a fourth input terminal, a first output terminal and a second output terminal, the first input terminal of the second modulation unit receives the third differential signal component, the second input terminal of the second modulation unit receives the fourth differential signal component, the third input terminal of the second modulation unit receives the third portion, the fourth input terminal of the second modulation unit receives the fourth portion, and the first output terminal of the second modulation unit is coupled to the second output terminal of the first modulation unit.

7. The biomedical signal sensing circuit as claimed in claim 6, wherein the amplifying unit comprises:
a first capacitor, having a first terminal and a second terminal, wherein the first terminal of the first capacitor is coupled to the first output terminal of the first modulation unit for receiving the first modulation signal;
a second capacitor, having a first terminal and a second terminal, wherein the first terminal of the second capacitor is coupled to the second output terminal of the second modulation unit for receiving the second modulation signal;
a third capacitor, having a first terminal and a second terminal, wherein the first terminal of the third capacitor is coupled to the second terminal of the first capacitor;
a fourth capacitor, having a first terminal and a second terminal, wherein the first terminal of the fourth capacitor is coupled to the second terminal of the second capacitor; and
an operational amplifier, having a first input terminal, a second input terminal, a first output terminal and a second output terminal, wherein the first input terminal of the operational amplifier is coupled to the second terminal of the first capacitor, the second input terminal of the operational amplifier is coupled to the second terminal of the second capacitor, the first output terminal of the operational amplifier is coupled to the second terminal of the third capacitor, and the second output terminal of the operational amplifier is coupled to the second terminal of the fourth capacitor.

8. The biomedical signal sensing circuit as claimed in claim 7, wherein the first modulation unit comprises:
a first transistor, having a first terminal, a second terminal and a control terminal, wherein the first terminal of the first transistor receives the first differential signal component, and the control terminal of the first transistor receives the second portion;
a second transistor, having a first terminal, a second terminal and a control terminal, wherein the first terminal of the second transistor receives the first differential signal component, and the control terminal of the second transistor receives the first portion;
a third transistor, having a first terminal, a second terminal and a control terminal, wherein the first terminal of the third transistor receives the second differential signal component, the control terminal of the third transistor receives the first portion, and the second terminal of the third transistor is coupled to the second terminal of the first transistor;
a fourth transistor, having a first terminal, a second terminal and a control terminal, wherein the first terminal of the fourth transistor receives the second differential signal component, the control terminal of the fourth transistor receives the second portion, and the second terminal of the fourth transistor is coupled to the second terminal of the second transistor,
wherein the second modulation unit comprises:
a fifth transistor, having a first terminal, a second terminal and a control terminal, wherein the first terminal of the fifth transistor receives the third differential signal component, and the control terminal of the fifth transistor receives the fourth portion;

a sixth transistor, having a first terminal, a second terminal and a control terminal, wherein the first terminal of the sixth transistor receives the third differential signal component, and the control terminal of the sixth transistor receives the third portion;

a seventh transistor, having a first terminal, a second terminal and a control terminal, wherein the first terminal of the seventh transistor receives the fourth differential signal component, the control terminal of the seventh transistor receives the third portion, and the second terminal of the seventh transistor is coupled to the second terminal of the fifth transistor; and an eighth transistor, having a first terminal, a second terminal and a control terminal, wherein the first terminal of the eighth transistor receives the fourth differential signal component, the control terminal of the eighth transistor receives the fourth portion, and the second terminal of the eighth transistor is coupled to the second terminal of the sixth transistor.

9. The biomedical signal sensing circuit as claimed in claim 8, wherein the third modulation signal comprises a first component and a second component, the first component is inverted to the second component, the first sensing signal comprises a third component and a fourth component, the third component is inverted to the fourth component, the second sensing signal comprises a fifth component and a sixth component, and the fifth component is inverted to the sixth component, wherein the first demodulation unit has a first input terminal, a second input terminal, a third input terminal, a fourth input terminal, a first output terminal and a second output terminal, the first input terminal of the first demodulation unit is coupled to the first output terminal of the operational amplifier to receive the first component, the second input terminal of the first demodulation unit is coupled to the second output terminal of the operational amplifier to receive the second component, the third input terminal of the first demodulation unit receives the first portion, the fourth input terminal of the first demodulation unit receives the second portion, the first output terminal of the first demodulation unit outputs the third component, and the second output terminal of the first demodulation unit outputs the fourth component, wherein the second demodulation unit has a first input terminal, a second input terminal, a third input terminal, a fourth input terminal, a first output terminal and a second output terminal, the first input terminal of the second demodulation unit is coupled to the first output terminal of the operational amplifier to receive the first component, the second input terminal of the second demodulation unit is coupled to the second output terminal of the operational amplifier to receive the second component, the third input terminal of the second demodulation unit receives the third portion, the fourth input terminal of the second demodulation unit receives the fourth portion, the first output terminal of the second demodulation unit outputs the fifth component, and the second output terminal of the second demodulation unit outputs the sixth component.

10. The biomedical signal sensing circuit as claimed in claim 9, wherein the first demodulation unit comprises:

a ninth transistor, having a first terminal, a second terminal and a control terminal, wherein the first terminal of the ninth transistor receives the first component, and the control terminal of the ninth transistor receives the second portion;

a tenth transistor, having a first terminal, a second terminal and a control terminal, wherein the first terminal of the tenth transistor receives the first component, and the control terminal of the tenth transistor receives the first portion;

an eleventh transistor, having a first terminal, a second terminal and a control terminal, wherein the first terminal of the eleventh transistor receives the second component, the control terminal of the eleventh transistor receives the first portion, and the second terminal of the eleventh transistor is coupled to the second terminal of the ninth transistor;

a twelfth transistor, having a first terminal, a second terminal and a control terminal, wherein the first terminal of the twelfth transistor receives the second component, the control terminal of the twelfth transistor receives the second portion, and the second terminal of the twelfth transistor is coupled to the second terminal of the tenth transistor, wherein the second demodulation unit comprising:

a thirteenth transistor, having a first terminal, a second terminal and a control terminal, wherein the first terminal of the thirteenth transistor receives the first component, and the control terminal of the thirteenth transistor receives the fourth portion;

a fourteenth transistor, having a first terminal, a second terminal and a control terminal, wherein the first terminal of the fourteenth transistor receives the first component, and the control terminal of the fourteenth transistor receives the third portion;

a fifteenth transistor, having a first terminal, a second terminal and a control terminal, wherein the first terminal of the fifteenth transistor receives the second component, the control terminal of the fifteenth transistor receives the third portion, and the second terminal of the fifteenth transistor is coupled to the second terminal of the thirteenth transistor; and a sixteenth transistor, having a first terminal, a second terminal and a control terminal, wherein the first terminal of the sixteenth transistor receives the second component, the control terminal of the sixteenth transistor receives the fourth portion, and the second terminal of the sixteenth transistor is coupled to the second terminal of the fourteenth transistor.

* * * * *